(12) United States Patent
Wu et al.

(10) Patent No.: US 8,977,339 B1
(45) Date of Patent: Mar. 10, 2015

(54) METHOD FOR ASSESSING STENOSIS SEVERITY THROUGH STENOSIS MAPPING

(71) Applicants: Zhongle Wu, Troy, MI (US); James P. Jacobs, Littleton, MA (US)

(72) Inventors: Zhongle Wu, Troy, MI (US); James P. Jacobs, Littleton, MA (US)

(73) Assignee: Intrinsic Medical Imaging LLC, Bloomfield Hills, MI (US)

( * ) Notice: Subject to any disclaimer, the term of this patent is extended or adjusted under 35 U.S.C. 154(b) by 0 days.

(21) Appl. No.: 14/098,125

(22) Filed: Dec. 5, 2013

(51) Int. Cl.
*A61B 5/05* (2006.01)
*A61B 5/02* (2006.01)
*A61B 6/00* (2006.01)
*A61B 5/021* (2006.01)
*A61B 5/107* (2006.01)
*A61B 6/03* (2006.01)
*A61B 8/08* (2006.01)
*A61B 5/00* (2006.01)
*A61B 5/026* (2006.01)

(52) U.S. Cl.
CPC ........... *A61B 5/02007* (2013.01); *A61B 6/5217* (2013.01); *A61B 5/021* (2013.01); *A61B 5/1075* (2013.01); *A61B 6/032* (2013.01); *A61B 8/5223* (2013.01); *A61B 5/7282* (2013.01); *A61B 8/0891* (2013.01); *A61B 5/0263* (2013.01); *A61B 5/02035* (2013.01); *A61B 6/504* (2013.01)

USPC .......... 600/408; 600/407; 600/410; 600/427; 600/429; 600/424

(58) Field of Classification Search
USPC .......................... 600/407, 410, 424, 427, 429
See application file for complete search history.

(56) References Cited

U.S. PATENT DOCUMENTS 8,496,594 B2 * 7/2013 Taylor et al. .................. 600/504

* cited by examiner

*Primary Examiner* — Joel Lamprecht
(74) *Attorney, Agent, or Firm* — Dickinson Wright PLLC

(57) ABSTRACT

A method of assessing stenosis severity for a patient includes obtaining patient information relevant to assessing severity of a stenosis, including anatomical imaging data of the patient. Based on the anatomical imaging data, the existence of any lesions of concerns may be identified. A three dimensional image can be generated of any irregular shaped lesion of concern and a surrounding area from the patient anatomical imaging data. A plurality of comparative two dimensional lesion specific models may be created that have conditions that correspond to the three dimensional model. The comparative two dimensional models may represent vessels having regular shaped lesions with each of the comparative two dimensional models represents a different stenosis severity. The three dimensional model can then be mapped to one of the plurality of comparative two dimensional models. After this mapping, a diagnosis of whether the patient has coronary artery disease may be made.

18 Claims, 6 Drawing Sheets

METHOD FOR ASSESSING STENOSIS SEVERITY THROUGH STENOSIS MAPPING

TECHNICAL FIELD

The present disclosure broadly relates to a method of accurately identifying and diagnosing coronary artery disease. More specifically, the present disclosure relates to a noninvasive method of accurately identifying and diagnosing coronary artery disease as it relates to irregular shaped lesions through stenosis severity mapping.

BACKGROUND OF THE INVENTION

Coronary artery disease (CAD) is a common type of heart disease and leading cause of death in the United States in both men and women. CAD is often caused when the arteries that supply blood to the heart muscle become hardened and narrowed permitting less blood to flow therethrough. When this occurs, the heart muscle cannot get the required blood and oxygen it needs, which can lead to chest pain or a heart attack. According to statistics, each year CAD affects some 16 million people in the U.S., causes approximately 1.2 million heart attacks, and over 450,000 deaths.

Early detection techniques and procedures have been developed in order to diagnose CAD and determine whether treatment is necessary. However, current diagnostic techniques are often equivocal, which results in a significant number of low to mid risk patients being unnecessarily admitted from emergency rooms to the hospital for further testing. After further testing, CAD is ruled out for many of these low to mid risk patients, which results in unnecessary costs exceeding $10 billon.

Invasive diagnostic techniques for CAD are known, but they are extremely expensive. One common invasive imaging technique is coronary catheter/angiography (CA). With CA, a catheter is inserted into a person's artery and a contrast agent or dye is injected into the artery. As the contrasted blood flows through the artery, any narrowing areas of a vessel can be readily seen, which can indicate the presence of plaque. Another known invasive imaging technique is intravascular ultrasound (IVUS), which involves the insertion of an IVUS catheter into a blood vessel. The catheter includes a transducer that emits a beam within the artery to gauge the location of the surrounding vessel. The resulting vessel shape that is determined can reveal the presence of any plaque. Another known invasive technique is optical coherence tomography (OCT), which is an interferometric technique that typically employs near-infrared light to capture three-dimensional images from within the artery to show the existence of any plaque.

Due to the cost and invasive nature of these techniques, non-invasive diagnostic techniques have been developed to assist in determining the existence of CAD. While these techniques are less expensive, they have limitations. One such increasingly employed technology is coronary computed tomography angiography (CCTA), which non-invasively obtains anatomic data of the vessel and surrounding structures for evaluation of the severity of artery stenosis. In general, CCTA gathers this data through high resolution cardiac imaging. The resultant imaging allows for the assessment of any luminal narrowing and/or atherosclerotic plaque that can cause the stenosis.

Armed with the CCTA data, there are various methods of assessing a coronary artery lumen for stenosis, including visual assessment and quantitative assessment of the stenosis. These methods can be performed manually, semi automatically or automatically on the CCTA data. Commonly used assessment methods include estimating the narrowed diameter of an artery (luminal diameter stenosis) or the narrowed artery area (luminal area stenosis) to grade the severity of stenosis. Such estimates generally involve defining clinically relevant coronary stenosis based on a predetermined percentage of luminal diameter stenosis or luminal area stenosis, i.e., 50%. Generally, the diagnostic performance of these methods provides good sensitivity and specificity for detecting significant severe stenosis.

However, in cases where intermediate stenosis lesions exist, the specificity and accuracy of this method is lower, despite its high negative prediction value. One known cause for this low specificity is that the luminal diameter stenosis and luminal area stenosis assessment techniques may lead cardiac surgeons to overestimate CAD severity similar to rates reported by cardiologists and radiologists. The overestimation of stenosis severity with CCTA may be affected by the assessment of the luminal diameter within the cross-section image since coronary arteries enlarge in response to athermanous plaque growth, a phenomenon referred to as "remodeling". The overestimation/underestimation and low specificity of stenosis severity may also be affected by the difficulty of luminal diameter assessment since irregular arterial lumen shapes are not uncommon at lesion sites. As such, the luminal diameter assessment technique may misrepresent true lumen narrowing in many instances, which does not solve the issue of unnecessary costs associated with accurately assessing the existence of CAD.

Figure 1:
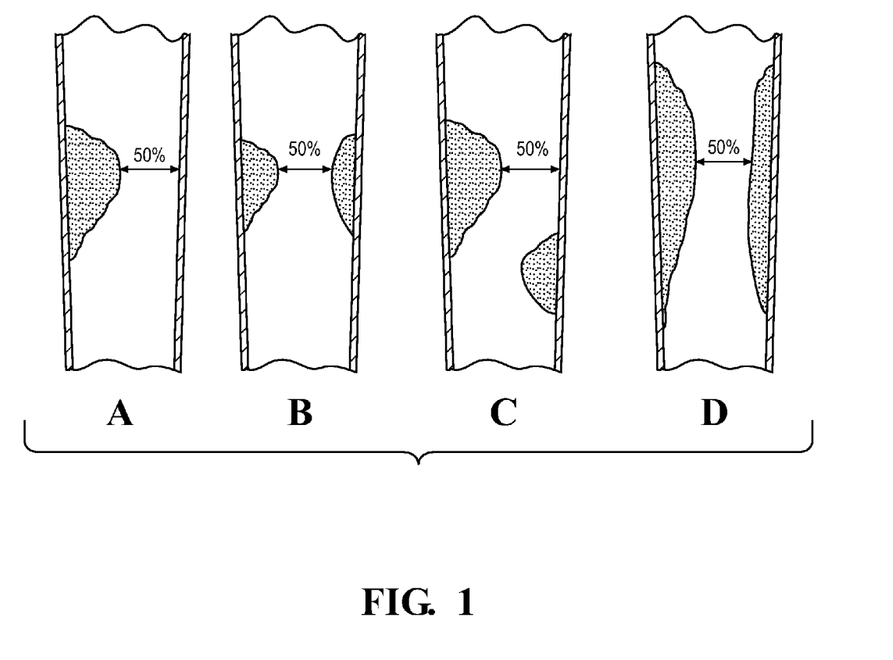
FIG. 1 is a schematic illustration of various examples of stenosis severity having different irregular shaped stenosis and a resulting luminal diameter of 50%.
Figure 2:
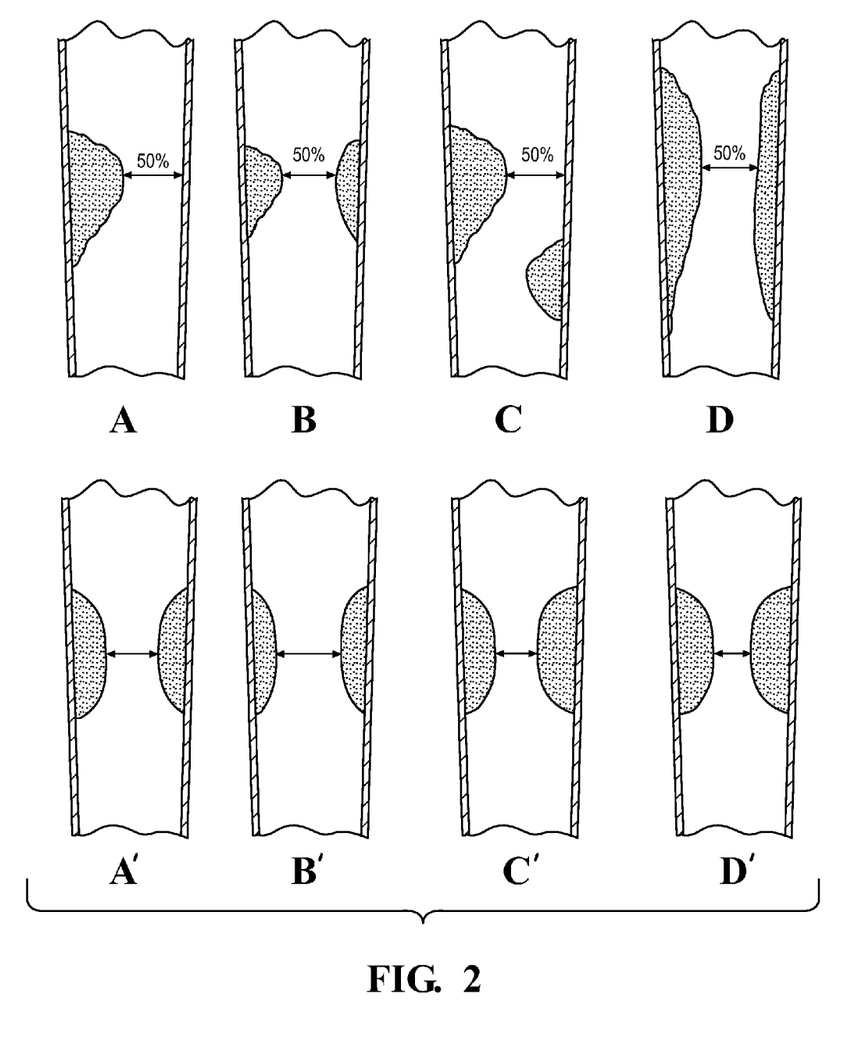
FIG. 2 is a schematic illustration of how each of the irregular-shaped stenosis examples of FIG. 1 correspond to regular shaped stenosis illustrations.

The difficulty with this assessment technique can be illustrated by the schematic diagram of FIG. 1, which depicts four examples (A) through (D) of different stenosis severity each having different geometries. Each of these examples illustrates a condition with a geometric luminal diameter stenosis of 50%. In other words, each of the examples illustrates an effective reduction in the vessel diameter to 50% at the narrowest point with lesions having different shapes, locations and/or sizes. FIG. 2 exemplarily illustrates how these different 50% luminal diameter stenosis can have different stenosis severities. As shown, examples (A) through (D) of FIG. 1 are mapped to illustrations of standard regular shaped stenosis having the same blood flow pressure drop from before the stenosis to after the stenosis. As shown, the examples in the bottom of FIG. 2, have different stenosis severities and thus illustrate the inaccuracy that can result when evaluating intermediate stenosis regions that have irregular shapes based on luminal diameter and luminal area techniques.

With recent advancements in blood flow hemodynamics, computational fluid dynamics (CFD) simulations have been successfully utilized to predict blood flow characteristics in arteries such as spatial and temporal variations of flow rate and pressure, to assist in diagnosing CAD. FFRct and virtual FFR are two recent examples where CFD has been used to predict the fractional flow reserve (FFR), which is defined as the pressure distal to a stenosis relative to the pressure before the stenosis, and thus the presence of CAD. FFR has been recognized as the gold standard for intermediate lesion assessment by the European Society of Cardiology. FFR measurement, however, is an invasive method where a pressure sensitive angioplasty wire is placed directly into the coronary artery through coronary catheterization. The FFRct method is complicated as it uses computational modeling on the CCTA for the whole coronary artery tree including a segment of the aorta artery. The virtual FFR method is similarly complicated as it uses computation modeling on the rotational coronary angiography (RoCA) images for the whole major vessel.

Both the FFRct and virtual FFR methods attempt to simulate the blood flow in physiologically realistic terms. This requires the estimation of sophisticated boundary conditions and initial conditions, which can be difficult to estimate accurately. In addition, computational modeling requires significant resources (both computational and labor) to segment the whole coronary artery tree domain or the whole vessel domain to construct the patient specific arterial lumen geometry as input to the CFD. This also requires a large domain of patient specific arterial models in order to perform simulations close to the physiological environment for accurately predicting FFR. The requirement of a large domain has various disadvantages. One disadvantage is that CFD simulation needs large computational resources as it is a computational insensitive algorithm. Another disadvantage is that the large domain requirement limits the number of CCTA scans that may be used due to the localized low image quality on a normal vessel. Additionally, imaging artifacts such as blurring of motion under limited temporal resolution of imaging, blooming artifacts from calcified plaques under limited spatial resolution of imaging, or even localized noise are more likely to appear in a large domain. This in turn reduces the confidence level of the prediction by the CFD simulation for FFR value.

Due to the limitations with the above treatment methods, a new technique for assessing stenosis severity would be beneficial.

SUMMARY OF THE INVENTION

It is therefore an aspect of the disclosure to provide an improved method for assessing luminal diameter stenosis.

It is another aspect of the disclosure to provide an improved method for assessing stenosis severity that is less expensive than prior methods.

It is a further aspect of the disclosure to provide an improved method for assessing stenosis severity that provides more meaningful assistance in clinically diagnosing CAD.

It is still another aspect of the disclosure to provide an improved method for assessing stenosis severity that is particularly suited for intermediate stenosis lesions.

It is still a further aspect of the disclosure to provide an improved method for assessing stenosis severity that is particularly suited for irregular shaped stenosis.

In accordance with the above and the other aspects, a method of assessing stenosis severity is provided. According to the method, a patient is imaged, which yields anatomical imaging data of the patient's heart and surrounding area. Next, the imaging data is reviewed to identify any lesions of concern. A three dimensional lesion specific model is then created of any lesions of concern. A plurality of lesion specific two dimensional models may then be created based on data relevant to the three dimensional specific model. Computational flow dynamic analysis is then performed on the flow path of the three dimensional model as well as the flow paths of each of the plurality of two dimensional models. Based on this computation, the two dimensional model that corresponds to the three dimensional model is then mapped thereto for analysis.

BRIEF DESCRIPTION OF THE DRAWINGS

Other aspects of the present disclosure will be readily appreciated, as the same becomes better understood by reference to the following detailed description when considered in connection with the accompanying drawings wherein.

DETAILED DESCRIPTION OF THE INVENTION

Figure 3:
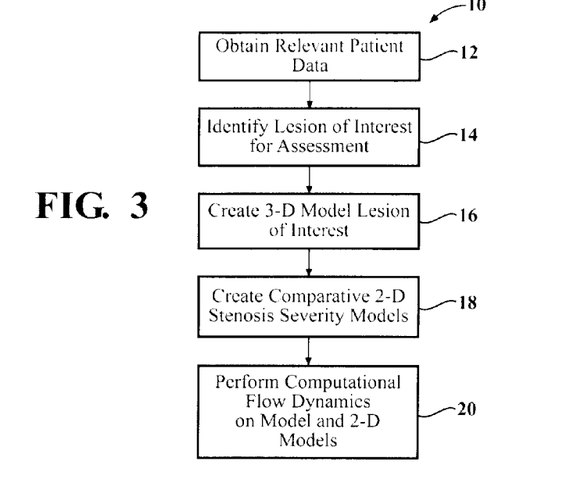
FIG. 3 is a block diagram of a method of determining stenosis severity in a human blood vessel in accordance with an aspect of the disclosure.

The present disclosure relates to a method of determining the stenosis severity of an artery and particularly as it relates to irregular-shaped stenosis. It will be appreciated, however, that the present disclosure applies to any type of shaped stenosis or any sized stenosis. FIG. 3 schematically illustrates a method 10 in accordance with an aspect of the present disclosure. According to an aspect, relevant data about a patient to be evaluated is initially obtained, as generally indicated by reference number 12. The relevant patient data may include patient anatomical data and particularly imaging data of the pertinent areas of concern. The patient anatomical data may be obtained by using a noninvasive imaging method such as CCTA. According to CCTA, a computed tomography (CT) machine may be used to scan images of structures, such as the heart region for diagnosis of the coronary artery vessels. The scanned data that results from this imaging method generally includes a stack of images that may then be assembled into a three-dimensional image, which may then be utilized for further diagnostics. Alternatively, other noninvasive three dimensional imaging methods such as magnetic resonance imaging (MRI) or ultrasound (US) may be used. Alternatively, invasive imaging methods, such as digital subtraction angiography (DSA) or rotational coronary angiography (RoCA) may also be used to image the structures of the patient's anatomy for further use. Other imaging methods may also be utilized.

According to an aspect, the relevant patient data that is initially obtained may also include other patient information that may assist with the assessment of stenosis severity. Such patient data may include a patient's blood pressure, heart rate, weight, hematocrit, or a variety of other patient information that may be relevant to stenosis severity assessment.

According to an aspect, after the patient data, including anatomical imaging information, is obtained, the next step may involve identifying a lesion of interest or concern for assessment, as generally indicated by reference number 14. According to this step, the obtained patient specific anatomical data that has been obtained from imaging as discussed above may first be evaluated to determine if the image quality is acceptable. The image quality evaluation may be performed by a user via a visual assessment. Alternatively, the image quality of the image anatomical data may be evaluated through a semi-automatic assessment using readily available imaging viewer software. Still further, the image quality may be assessed automatically using a computer system. If the quality is not acceptable, the image anatomical data may be reacquired using any of the methods above. Once acceptable image anatomical data is acquired, an analysis can be performed to determine whether there are any lesions of interest and their locations. The identification of any lesions of interest may be performed by visual inspection. Alternatively, this step may be performed by or with the assistance of a computer system.

As shown, after a lesion of interest has been identified, according to an aspect, a three-dimensional (3D) model of the lesion of interest may then be created, as generally indicated by reference number 16. It will be appreciated that if multiple lesions of interest exist, a corresponding number of 3D models may be created. According to another aspect, the method may be particularly suited for lesions having an irregular shape.

The 3D model of the identified lesion of interest may be created based on the anatomical image data using conventional software, such as 3D Slicer (www.slicer.org) or customized software such as Applicant's Spectrum Cardio Workstation. To create the 3D model, the luminal structure of the identified lesion together with the proximal and distal segments of the associated vessel may be segmented using various methods. According to one aspect, the segmentation may be performed automatically by a computer system, or semi-automatically by a user with seeding and correction. The 3D model may also be created by manual segmentation. According to an aspect, the segmentation may be performed in two steps. First, the centerline information of the luminal structure of interest may be extracted. Second, the luminal structure around the extracted centerline may be segmented. The segmented luminal structure of interest can then be generated and saved in a digital representation.

Figure 4:
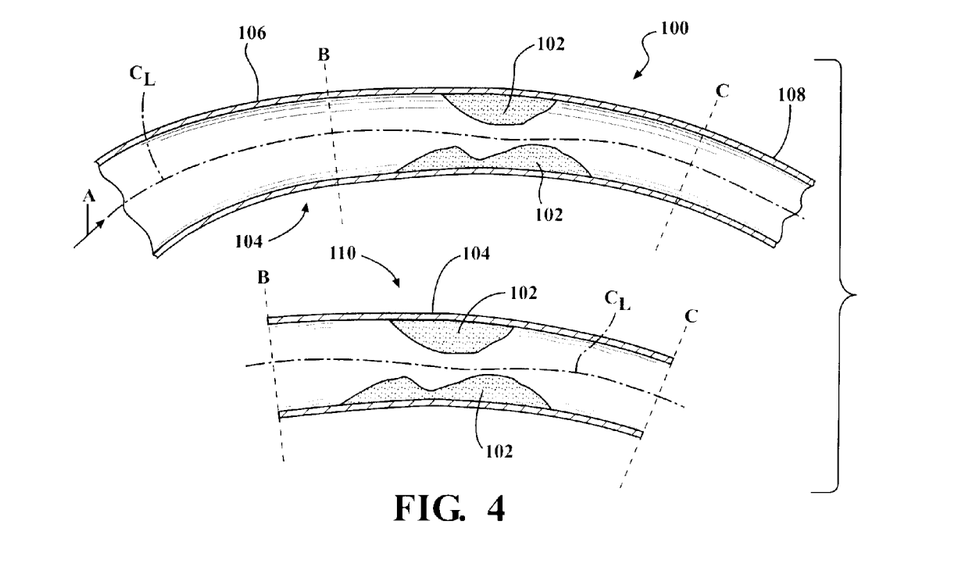
FIG. 4 is a schematic illustration of a step of building a three dimensional model from patient imaging data in accordance with an aspect of the disclosure.

FIG. 4 schematically illustrates the step of creating an exemplary 3D model from the image data 100. As shown, the image data may include an irregularly shaped stenosis 102 disposed within an artery 104 having a centerline $C_L$. The direction of blood flow in the image data is generally indicated by the arrow A. As shown, the artery 104 may include a proximal section 106 before the stenosis 102 and a distal section 108 after the stenosis 102. The image data reflects the location of the stenosis in the vessel and the shape of the stenosis.

According to an aspect, a lesion specific 3D model may then be created from the image data 100. Unlike prior processes, the 3D model according to the present disclosure need only include the artery luminal boundary around the lesion and nearby normal artery. Initially, with reference to FIG. 4, in the lesion specific 3D model 110, the extent of the lesion 102 along the artery vessel 104 may be estimated. Additionally, the image data 100 of the vessel 104 may include the lesion segment 102 as well as the non-diseased proximal segment 106 before the lesion and the non-diseased distal segment 108 after the lesion. As part of the preparation of the lesion specific 3D model 110, the lengths of the non-diseased proximal segment 106 and the non-diseased distal segment 108 may be shortened, as generally indicated by the dashed lines B and C. As shown in the lower portion of FIG. 4, the proximal and digital segments 106, 108 have been shortened in the model 110.

Figure 5A:
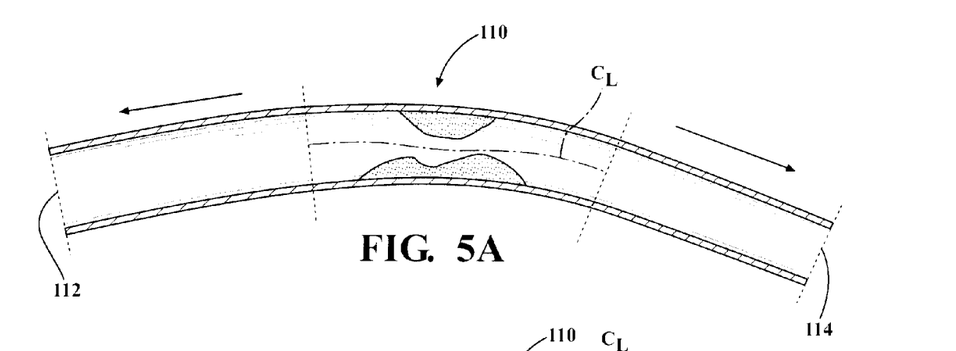
FIG. 5a is a schematic illustration of a step of extending an inlet and outlet of a lesion specific three dimensional model in accordance with an aspect of the disclosure.
Figure 5B:
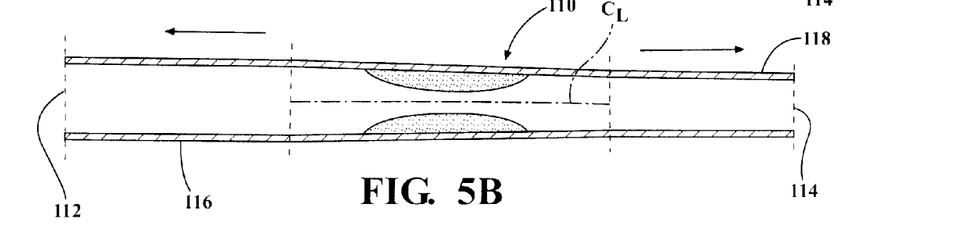
FIG. 5b is a schematic illustration of an exemplary two dimensional model with an extended inlet and outlet in accordance with an aspect of the disclosure.

Once the 3D lesion specific model 110 has been created as depicted in FIG. 4, the model 110 may be further prepared and processed. For example, according to an aspect, the generated model 110 may be preprocessed such as by smoothing and trimming. For example, the created 3D image model 110 may have an arcuate or non-linear shape, as depicted in FIG. 5a where the $C_L$ is not linear and the inlet and outlet boundaries are angled. As part of the preprocessing, the 3D image model 110 may be smoothed so that the inlet and outlet boundaries 112, 114 are perpendicular to the $C_L$ of the segment 104 as well as the walls of the vessel as schematically illustrated in FIG. 5b. Also, the centerline of the vessel $C_L$ may be made linear.

According to an aspect, the model 110 may then be super sampled to a high resolution to prepare it for CFD simulation, which has a high degree of accuracy. Additionally, the model 110 may also be initially represented by surface mesh and then be converted to a solid mesh composed of tetrahedrons to allow for the performance of CFD simulation using finite element method (FEM). According to another aspect, the model 110 may be initially represented by voxel and may then be converted to regular grid mesh for performing CFD simulation using lattice Boltzmann method (LBM).

Figure 6:
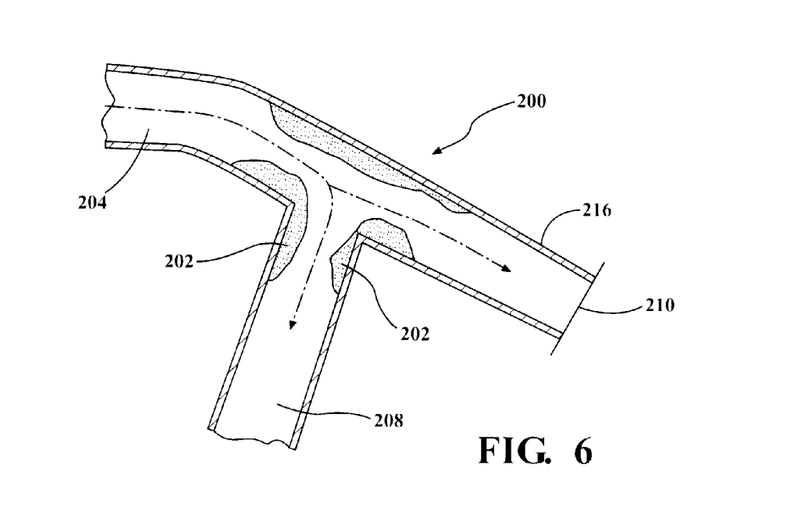
FIG. 6 is a schematic illustration of a step of evaluating a multiple outlet boundary condition in accordance with an aspect of the disclosure.

It is not uncommon for a lesion of interest 202 to be distributed across an area 200 having multiple outlet branches, as generally depicted in FIG. 6. As schematically illustrated in FIG. 6, the lesion 202 may be located in an area having an inlet flow path 204 that feeds a first outlet path 206 and a second outlet path 208. According to an aspect, when this condition is present, a 3D model may be created with only one inlet and one outlet. By this method, flow paths for each combination of inlet and outlets may be determined. According to another aspect, this can be accomplished by creating a virtual wall 210 to close off flow through the first outlet 206. A 3D model having a flow path from the inlet 204 to the second outlet 208 past the lesion may then be created for analysis. Similarly, a second 3D model may be created where a virtual wall is created in the second outlet 208 such that flow therethrough is blocked. The second model could thus allow for analysis of flow from the inlet 204 through the first outlet 206 past the lesion of interest 202.

In accordance with an aspect, if either or both of the inlet distance before the diseased lesion and the outlet distance after the diseased lesion are too short in the 3D model, estimating the boundary conditions may be difficult due to flow turbulence nearby the non-regular shape of the lesion causing unstable distribution of flow pressure and velocity at the inlet and outlet boundary layers. According to an aspect, in order to create stable flow at the inlet and outlet and assign boundary conditions, the inlet and outlet sections of the 3D model may be extended to a desired range in the manner discussed and schematically illustrated in FIG. 5b. According to an aspect, the extended inlet 116 and outlet 118 may be created as a circle and connected to the original shape of the captured inlet and outlet with a smooth transition being created between these geometries. According to a further aspect, for each flow path, the inlet and outlet area and the centerline distance may be determined. The extended inlet 116 and outlet 118 also is helpful for setting up the boundary condition due to the circle shape of the extended inlet 116 and outlet 118.

It will be appreciated that more, less or different processing steps may be employed to ready the 3D image 110 for further analysis in accordance with an aspect of the disclosure.

Once the 3D model 110 is processed and prepared, a list of known comparative lesion specific 2D stenosis severity mapping models 300 may be created as generally designated by reference number 14. As shown schematically in FIG. 7, the models 300a-300n may be constructed with regular shapes and different stenosis severity levels for each flow path to represent different levels of occlusion. For example, the various models could be created to represent stenosis severities from 5% to 95% with a different model for each 5% increment. The models 300 may be created and organized in increasing or decreasing stenosis severity. According to an aspect, the comparative lesion specific stenosis severity mapping models 300 may be generated based on the parameters discussed above as well as control parameters for different severity. As shown, the severity mapping models 300 may be depicted as straight pipelines with cross-sections that are circular in shape. As such, the simulated flow passing through each of the comparative models 300 may also have a circular symmetry which can be used to simplify the models to two dimensional. Any number of models 300 may be created and can be identified by numbers 1 through N.

Figure 7:
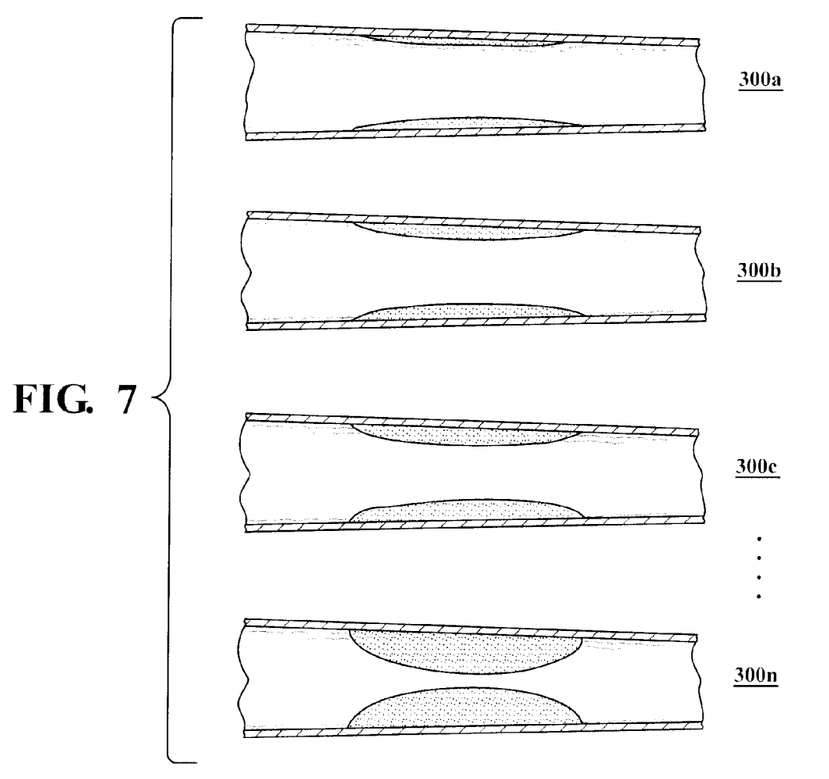
FIG. 7 is a schematic illustration of a step of creating a plurality of representing two dimensional models in accordance with an aspect of the disclosure.

In accordance with the disclosure, the 2D comparative models 300 may be created utilizing various control parameters so that the conditions between the 3D model and 2D models are as close as possible. One control parameter may be lesion location, which may be generally estimated based on the location of the lesion in the 3D lesion specific model 110 with respect to the centerline. Another control parameter may be lesion length. The lesion length may also be estimated based on the length of the lesion in the 3D lesion specific model 110 with reference to the centerline by measuring the length of the lesion between the start of the cross-section and the end of the cross-section of the vessel.

Another control parameter may be bump height. According to an aspect, the bump height of the lesions on one or both sides of the vessel is an important control parameter for stenosis severity of the lesion when an irregular shaped lesion is transferred to a regular shape. According to an aspect, the bump heights may be in the range between 0 to the radius at the lesion location in the 2D models. Because the inlet radius and the outlet radius in the 2D models may not be the same, the location of the radium used to estimate bump heights may be the center of the base of the regular bump shape on the vessel wall. The comparative models with different stenosis severity may be controlled by varying the bump heights. For example, N comparative models may be created with bump heights designated [B0, B1 ... BN−1], where $B_i = i*R/N$ with the variable R being the radius at the location of lesion.

A further control parameter may be the inlet radius and the outlet radius of the vessel. According to an aspect, the inlet and outlet radius may be estimated from the area of cross-section at the inlet and the outlet in the lesion specific 3D model 110. The method discussed above with respect to the 3D models for extending the inlet and outlet paths may be used to extend the inlet and outlet in the 2D models to obtain the same centerline length as the 3D models.

Figure 8:
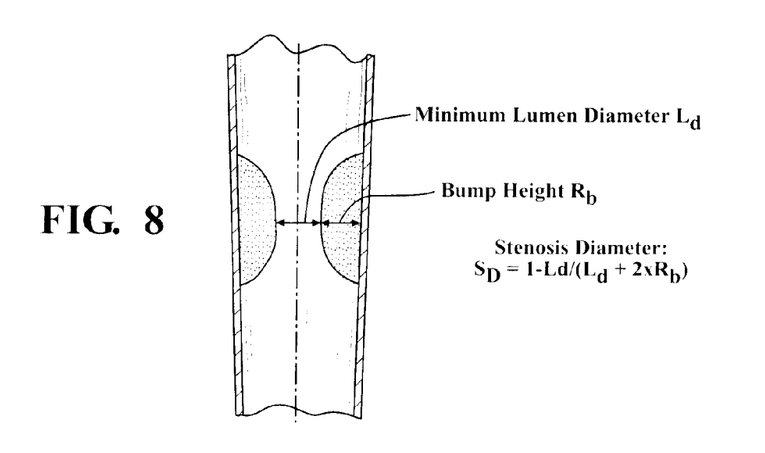
FIG. 8 is a schematic illustration of a stenosis severity mapping model utilizing stenosis diameter in accordance with an aspect of the disclosure.

Based on these control parameters, each of the 2D models is created and bumps or lesions may be created on both sides of the vessel wall in each of the severity 2D models with the bumps having different sizes. According to an aspect, the bump surface may be constructed by a U-shaped curve (quadratic curve) having a stenosis radius. According to another aspect, the stenosis radius for each model may be determined as the percentage of the bump height to the vessel radius, as schematically shown in FIG. 8. Other methods for determining the stenosis radius may also be utilized.

According to an aspect, vessel wall boundary conditions for the lesion specific flow path of the 3D model and 2D models can be determined. Pursuant to one aspect, a non-slip rigid wall boundary condition may be used at the wall layer, where the fluid velocity is zero at the contact to the wall. This is a simple boundary condition for the CFD simulation. However, other suitable boundary conditions may be employed.

The pressure at the outlet is estimated based on measured patient's systolic and diastolic blood pressure. The velocity at the inlet comes from the estimated flow rate which involves selection of a typical blood flow velocity at the outlet and an estimate of the area ratio between the inlet and the outlet. The area ratio between the inlet and the outlet may be derived from the 3D model. According to another aspect, inlet and outlet boundary conditions for the 3D models and the 2D models may next be determined. A simple velocity inlet, pressure outlet boundary condition may be used. As an example, the pressure at the outlet can be estimated by taking the average pressure of the measured patient's systolic and diastolic blood pressure. However, other suitable outlet pressures may be selected. The inlet flow velocity may be selected based on a distribution of fluid speed at the inlet cross-section. The velocity profile can be parabolically distributed as a fully developed boundary condition. According to a uniformly distributed velocity profile, the average velocity at the inlet may be estimated based on an expected flow rate at the outlet. The expected flow rate in the normal vessel without any lesion occlusion at the outlet can then be estimated by typical blood flow velocities in the coronary arteries when the patient is at rest. Given the flow rate at the inlet, the parabolic velocity profile can be derived easily because the extended inlet is a circle. The 2D severity chart models also utilize the same initial condition for the inlet and outlet that was determined for the 3D model. According to an aspect, the inlet and outlet diameters may be selected to compensate for any difference in the inlet versus outlet area that can occur in the normal vessel around the lesion. By way of example, the outlet diameter may be selected to be 1% smaller than the inlet diameter to account for this variation.

If the 3D lesion specific model has multiple outlets, the severity mapping models may have a single inlet and outlet for each flow path. As discussed above, all other outlets may be treated as a solid wall so no flow occurs through those outlets. Using a single inlet and outlet and blocking all other outlets not only simplifies the outlet boundary condition estimation for CFD simulation, but also removes any effect from flow through the other outlets. This step allows severity mapping models to represent the flow path in the 3D lesion specific model.

According to an aspect, the next step of the method may involve performing computational flow dynamics on each flow path as generally indicated by reference number 20. Specifically, CFD simulations may be performed on the 3D lesion specific model 110 as well as on the various 2D comparative models 300. The CFD simulation may be done with off the shelf software, such as OpenFoam (www.openfoam.com), Palabos (www.palabos.ort), conventional CFD software or custom developed software. Each simulation may yield a value for the force required to push the blood flow through the lesion given flow momentum where the force is the pressure drop between the inlet and the outlet. According to an aspect, the CFD simulation may also utilize fluid blood flow characteristics, such as blood density and viscosity. Typical blood density and viscosity values may be used. Upon completion of the CFD simulations, the pressure at the inlet will be obtained and the dropped pressure between the inlet and outlet may be calculated for the 3D model as well as all of the 2D models.

Figure 9:
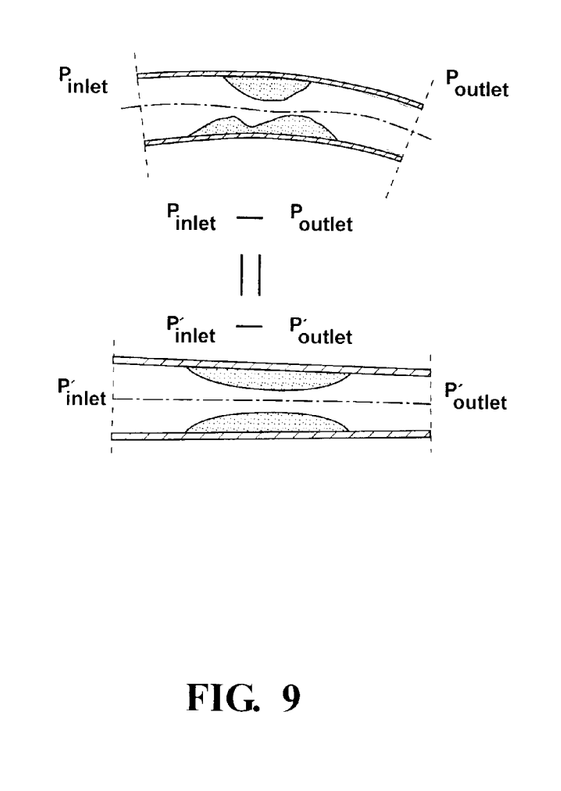
FIG. 9 is a schematic illustration of the step of mapping a three dimensional lesion specific model to a two dimensional model in accordance with an aspect of the disclosure.

After the CFD simulations on the 3D irregular model and all 2D regular models have been completed, the 3D irregular model may be mapped to one of the 2D comparative models, as schematically shown in FIG. 9. This may be done by finding the specific 2D model that has the same pressure drop as the 3D lesion specific model. According to an aspect, the dropped pressure values of the 2D regular models may be used to create a pressure dropping curve of the 2D severity models. With the dropped pressure value of the 3D model, the proper 2D model may be determined based on the location where the 3D dropped pressure value intersects on the created 2D curve. The mapped 2D model will be the nearby severity model.

Once the severity mapping location has been obtained, the bump height may be interpolated within the nearby 2D models. With this information, a new 2D equivalent regular model may be generated based on the estimated bump height and the stenosis radius is obtained.

Note that not all of the activities described above in the general description or the examples are required, that a portion of a specific activity may not be required, and that one or more further activities may be performed in addition to those described. Still further, the orders in which activities are listed are not necessarily the order in which they are performed.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Many other embodiments may be apparent to those of skill in the art upon reviewing the disclosure. Other embodiments may be used and derived from the disclosure, such that a structural substitution, logical substitution, or another change may be made without departing from the scope of the disclosure. Accordingly, the disclosure is to be regarded as illustrative rather than restrictive.

Certain features are, for clarity, described herein in the context of separate embodiments, may also be provided in combination in a single embodiment. Conversely, various features that are, for brevity, described in the context of a single embodiment, may also be provided separately or in any sub combination. Further, reference to values stated in ranges includes each and every value within that range.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The above-disclosed subject matter is to be considered illustrative, and not restrictive, and the appended claims are intended to cover any and all such modifications, enhancements, and other embodiments that fall within the scope of the present invention. Thus, to the maximum extent allowed by law, the scope of the present invention is to be determined by the broadest permissible interpretation of the following claims and their equivalents, and shall not be restricted or limited by the foregoing detailed description.

Although only a few exemplary embodiments have been described in detail above, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

What is claimed is:

1. A method of assessing stenosis severity for a patient, comprising:
    obtaining patient information relevant to assessing stenosis severity, including anatomical imaging data of the patient;
    identifying the existence of any lesions of concern in a vessel of the Patient that have an irregular shape from the anatomical imaging data;
    inputting the anatomical imaging data of the patient into a computer system;
    utilizing a processor associated with the computer system and task specific software to generate a three dimensional model from the patient anatomical imaging data of at least one lesion of concern within the vessel, wherein the generated three dimensional model includes a vessel inlet, the at least one lesion of concern, and at least one vessel outlet;
    utilizing the processor and task specific software to create a series of comparative two dimensional lesion specific models having conditions that correspond to the three dimensional model, wherein each of the series of comparative two dimensional models represents a vessel having one or more regular shaped lesions within the vessel and wherein each of the two dimensional lesion specific models includes differently configured lesions each representing a different known level of stenosis severity;
    mapping the three dimensional model to one two dimensional model of the series of comparative two dimensional models;
    deriving a quantitative measure of stenosis severity of the patient's coronary artery disease based on the mapped two dimensional model.

2. The method of claim 1, wherein the task specific software employs segmentation of the patient anatomical imaging data to create the three dimensional model from the patient anatomical imagine data.

3. The method of claim 1, wherein the three dimensional model consists of the at least one lesion of concern located within the vessel and wherein the vessel includes a section of vessel between the vessel inlet and the lesion and a section of vessel between the lesion and the vessel outlet.

4. The method of claim 1, wherein the step of mapping further comprises performing computational fluid dynamics on the three dimensional model and each of the series of comparative two dimensional models.

5. The method of claim 4, wherein the step of performing computational fluid dynamics involves selecting one or more of the following parameters: blood pressure at the inlet, a plurality of vessel diameters along the three dimensional model, a plurality of vessel diameters along the two dimensional models, blood viscosity, blood velocity, blood flow rate, vessel elasticity, vessel calcification, and differences between two dimensional models derived from a plurality of phases of the heartbeat.

6. The method of claim 1, further comprising:
utilizing task specific software to preprocess the patient anatomical imaging data prior to the step of generating the three dimensional model.

7. The method of claim 6, wherein the step of preprocessing the anatomical imaging data includes determining whether the anatomical image data for the at least one lesion of interest, includes multiple outlets; and
identifying a single inlet and a single virtual outlet from which to create the three dimensional model.

8. The method of claim 7, further comprising:
reducing the multiple outlets on the anatomical imagine data for the vessel including the at least one lesion of interest to a single virtual outlet for further processing.

9. The method of claim 8, further comprising:
manipulating the anatomical imaging data to reduce the multiple outlets to the single virtual outlet by virtually closing off any flow paths to the other multiple outlets that are not the identified single virtual outlet such that the anatomical imaging data for the at least one vessel of interest has the vessel inlet and the vessel outlet.

10. The method of claim 6, further comprising:
smoothing the anatomical image data such that a centerline of a vessel containing the at least one lesion of interest is linear and such that the vessel inlet and the vessel outlet are perpendicular to the centerline.

11. The method of 6, wherein the vessel inlet and the vessel outlet may be assigned a circular shape with each having a diameter that corresponds to an area of the opening in the anatomical image data.

12. The method of claim 1 wherein the step of creating a plurality of comparative two dimensional models includes utilizing a plurality of control parameters to assist in having the two dimensional comparative models properly reflect the three dimensional model.

13. The method of claim 12, wherein the plurality of control parameters include one or more of the following: lesion location, lesion length, bump height, inlet radius and outlet radius.

14. The method of claim 12, wherein the step of mapping the three dimensional model to one of the two dimensional models includes predicting a pressure drop across the lesion of interest from computational fluid dynamics.

15. The method of claim 14, wherein the predicted pressure drop across the three dimensional model and the plurality of two dimensional models is a statistical result from a plurality of calculations using a range of possible control parameters including: inlet blood flow, blood pressure, blood velocity, and blood density.

16. The method of claim 1, wherein the quantitative measure of stenosis severity is reported as at least one of the following: effective percent reduction in vessel diameter or effective percent reduction in vessel area.

17. The method of claim 1, wherein the patient information consists of one or more of Cardiac Computed Tomography Angiography (CCTA) data sets.

18. The method of claim 1, wherein the patient information consists of one or more data sets derived from one or more of the following: magnetic resonance angiography (MRA), ultrasound (US), digital subtraction angiography (DSA), or rotational coronary angiography (RoCA).

* * * * *

UNITED STATES PATENT AND TRADEMARK OFFICE
CERTIFICATE OF CORRECTION

| | | |
|---|---|---|
| PATENT NO. | : 8,977,339 B1 | Page 1 of 1 |
| APPLICATION NO. | : 14/098125 | |
| DATED | : March 10, 2015 | |
| INVENTOR(S) | : Zhongle Wu et al. | |

It is certified that error appears in the above-identified patent and that said Letters Patent is hereby corrected as shown below:

In the claims

Column 10, line 49, Claim 2, imagine should read – "imaging".

Signed and Sealed this
Twenty-second Day of December, 2015

Michelle K. Lee
*Director of the United States Patent and Trademark Office*